(12) United States Patent
Calbo et al.

(10) Patent No.: US 8,656,757 B2
(45) Date of Patent: Feb. 25, 2014

(54) APPLANATION SYSTEM FOR EVALUATION OF CELL PRESSURE DEPENDENT FIRMNESS ON LEAVES AND SOFT ORGANS FLAT FACE SEGMENTS

(75) Inventors: Adonai Gimenez Calbo, Sao Carlos (BR); Jose Dalton Cruz Pessoa, Sao Carlos (BR)

(73) Assignee: Empresa Brasileira de Pesquisa Agropecuaria—Embrapa, Plano Piloto (BR)

( * ) Notice: Subject to any disclaimer, the term of this patent is extended or adjusted under 35 U.S.C. 154(b) by 389 days.

(21) Appl. No.: 12/669,320

(22) PCT Filed: Jul. 16, 2008

(86) PCT No.: PCT/BR2008/000205
§ 371 (c)(1), (2), (4) Date: Aug. 16, 2010

(87) PCT Pub. No.: WO2009/009850
PCT Pub. Date: Jan. 22, 2009

(65) Prior Publication Data
US 2010/0311100 A1    Dec. 9, 2010

(30) Foreign Application Priority Data
Jul. 16, 2007  (BR) ..................................... 0705830

(51) Int. Cl.
*G01M 3/02*    (2006.01)
(52) U.S. Cl.
USPC ............................................................ 73/37

(58) Field of Classification Search
USPC ............................................................ 73/37
See application file for complete search history.

(56) References Cited

U.S. PATENT DOCUMENTS 6,212,941 B1 *    4/2001    Cholet ............................. 73/38

FOREIGN PATENT DOCUMENTS

| DE | 37757 B | 5/1965 |
| DE | 698 28 264 T2 | 12/2005 |
| EP | 0 267 737 A2 | 5/1988 |
| EP | 0 409 784 A1 | 1/1991 |

* cited by examiner

*Primary Examiner* — Hezron E Williams
*Assistant Examiner* — Rodney T Frank
(74) *Attorney, Agent, or Firm* — Alston & Bird LLP

(57) ABSTRACT

The applanation system on air permeated screen (1) of this invention is a versatile instrument for measurement of tissue firmness generated by cell turgor pressure of leaves and organs segments with thin and elastic cell wall of several stalk, leaves, fruits and roots. It is composed by an air source with adjusted maximum flow (6), a porous element (2) inserted on a screen (1), by which air flows, and a device for compression application (4). For measurements, the organ is progressively pressed against the screen until reversible interruption of the air flow crossing the porous element (2) is indicative of adequate applanation of the leaf against the screen. In this condition, one takes the firmness measurement reading as the applanation pressure (5). This firmometer enables postharvest quality evaluation and measurements for ecophysiology studies and irrigation management procedure benchmarking.

4 Claims, 4 Drawing Sheets

APPLANATION SYSTEM FOR EVALUATION OF CELL PRESSURE DEPENDENT FIRMNESS ON LEAVES AND SOFT ORGANS FLAT FACE SEGMENTS

FIELD OF THE INVENTION

The present invention refers to a system developed to measure the cell turgor pressure dependent firmness of leaves and planar segments of organs having parenchymal, thin and flexible cell walls, for applications in ecophysiology, irrigation management benchmarking and in post-harvest quality assessment of leaves and segmented products. In this system the samples are gradually compressed against a screen having inserted or engraved a porous element by which an air flow is crossed. As soon as this compression becomes sufficient for the organ obstruction of the air flow, then the organ was applanated against the screen. In this condition, reversible, the read pressure is the firmness measure. This system is simple and enables the construction of portable instruments to measure the cell turgor pressure depending firmness.

BACKGROUND OF THE INVENTION

The applanation technique has been used at least since 1957 when was developed the Goldman tonometer for ophtalmologyc use (see Amaral et al. Arquivos Brasileiros de Oftalmologia 69:41-45, 2006). In plants, Berstein & Lustig (see Vitis 20:15-21, 1981; Scientia Horticulturae 25:129-136, 1985) were pioneers in the use of this technique on grape berries and on others similar juicy fruits. Calbo & Calbo (see Revista Brasileira de Fisiologia Vegetal 1:41-45, 1989) has extended the principles of this measurement, which was applied to organs that could be treated as a membrane surrounded sphere, for other convex organs with regular and parenchymal dermal tissue. Two simple applanator models and one fast procedure for kneaded area evaluation were developed by Calbo & Nery (see Horticultura Brasileira 12:14-18, 1995), together with some contour conditions attended for cell turgidity dependent firmness measurements validation.

The reversible cell deformation occurrence during firmness measurements by applanation technique were subsequently evidenced (see Calbo et al. Annals of Botany 76:365-370, 1995; Pereira & Calbo Pesquisa Agropecuária Brasileira 35:2429-2436, 2000). Additionally, Calbo & Nery (see Brazilian Archives of Biology and Technology 44:41-48, 2001) have shown that for some cellular arrangement types may have simple mathematics relationship between firmness measured with applanation technique and the cell turgor pressure on tissues having thin cell wall, measured by intercellular gaseous volumes percent initially contained in the tissues.

Nowadays the firmness measure of fruits and vegetables by applanation has been used, mostly in Brazil, because it is a firmness measure dependent of physiology and of the hydric state of the plant which can be made repeatedly in a same organ. Then for genotypes selection, Andrade et al., (see Pesquisa Agropecuária Brasileira 40:555-561, 2005) have developed a criterion for determination of conservation half-life for tomato fruits enabling fruits selection with bigger storage capacity. This statistics technology can be extended to several other climacteric fruits. For guava and mango the applanation technique has been used for determination of firmness lost of these fruits caused by maturing. In vegetables as eggplant, beet (see Kluge et al. Scientia Agrícola 56:1045-1050, 1999) and carrot (see Calbo Bragantia 59:7-10, 2000; Caron et al. Horticultura Brasileira 21:597-600, 2003) the applanation technique has been used to determine firmness lost caused by transpiration during storage. For engineering purposes firmness measurements of fruits and vegetables by applanation technique together with the use of a simple mathematic model have turned possible determining the maximum height for product stacking and determining the package maximum height for the majority of fruits and vegetables marketed in Brazil (see Luengo et al. Horticultura Brasileira 21:704-707, 2003; Luengo, Doctorade Thesis, Escola Superior de Agricultura Luiz de Queiroz, Piracicaba, 77 p, 2006).

The applanation technique as described by Calbo & Nery (see Horticultura Brasileira 12:14-18, 1995) applies to firmness measurement of convex organs with regular and parenchymal dermal tissue. Then organs with irregularities, laminar organs and segmented organs require the development of specific procedures for their suitability measurement. For these applications, a porous tip applanation system for the application of applanation technique was tested for the comparison of water-lack stress effects during lettuce cultivation in pot (see Calbo III Congresso Brasileiro de Fisiologia Vegetal, Viçosa, 1991). Despite promising, the obtained results with that applanation system resulted in an expressive deformation of the leaf on the porous tip edge (2), reason why the use of that type of instrument was interrupted.

Systems in which compression applies can also be used for other purposes. Then, Shayo-Ngowi & Campbell (see Agronomy Journal 72:567-568, 1980) developed "hydraulic press" for water tension estimation on leaves and segmented tissues. For this type of segments measurement, typically with 25 $mm^2$ area and up to 3 mm thickness, segments are compressed under the transparent glass plate until sap start exit from the compressed segment vascular bundles. According to Eldrege & Shock (see American Potato Journal 67:307-312, 1990) the method "hydraulic press" has presented a good correlation with the water tension measured with the pressure chamber on potatoes leaves. This author however draws attention to the lack of theoretical basis for the use of the "hydraulic press", deficiency that is actually partially overcame by the developments showed in the works of Calbo et al. (see Annals of Botany 76:365-370, 1995) and Calbo & Nery (see Brazilian Archives of Biology and Technology 44:41-48, 2001).

The leaves' firmness measurement, on the other hand, has been considered not well resolved. An alternative for the firmness leaves hydration dependent measurement was described by Heathcote et al. (see Journal of Experimental Botany 30:811-816, 1979). On the test tip having a round cavity, the leaf surface deformation was induced by pressing a stick centralized on the leaf blade. Alternatively the leaf was pressed with a plate, acting in the middle of parallel bars, against which the leaf was supported. The distance between these bars must be as bigger as thicker and harder is the leaf. As described by Turner & Sobrado (see Journal of Experimental Botany 34:1562-1568, 1983), this type of method is sensitive to the leaf blade thickness and hence is difficult the comparison between different leaves, even being of one unique plant. Additionally the irregularities and veins distribution are important variation sources for the use of analog methods as recommended by Heathcote et al. (see Journal of Experimental Botany 30:811-816, 1979).

In this invention, it is described a novel applanator type for firmness measurement dependent of leaves cell turgor and of planar segments of organs which solve the majority of the limitations presented by the systems previously developed. This new applanation system makes use of a screen containing a porous element by which air flows, and due to its compression system it is useful for firmness measurement of leaves and planar segments of organs, as fruits and vegetables, since they are made of soft tissues where the firmness is modulated by the turgor pressure inside cells having fine structure cell walls.

SUMMARY OF THE INVENTION

The on screen applanation system (1) air permeate in a porous element (2) of this invention is an instrument for firmness tissue measurement generated by the cell turgor pressure on leaves and laminar segments or organs with elastic and parenchymatous cell walls of segmented fruits and vegetables. The system is composed by an air source with low pressure (6) from where leaves an air flow adjusted in a restriction (13), for a screen (1) with a porous element (2) from where air flows and one device for apply and measure the applied compression (5). For the measurement, the organ is pressed progressively by a membrane (4), until the air flow through the porous element (2) on the screen (1) is interrupted by the applanation of the organ surface (3). The reading of this lower pressure which stops the air flow, in a reversible manner, is the firmness measure. This applanation system is a device for postharvest quality assessment, for ecophysiological studies and for the benchmarking of irrigation management practices.

DETAILED DESCRIPTION OF THE INVENTION

Figure 1:
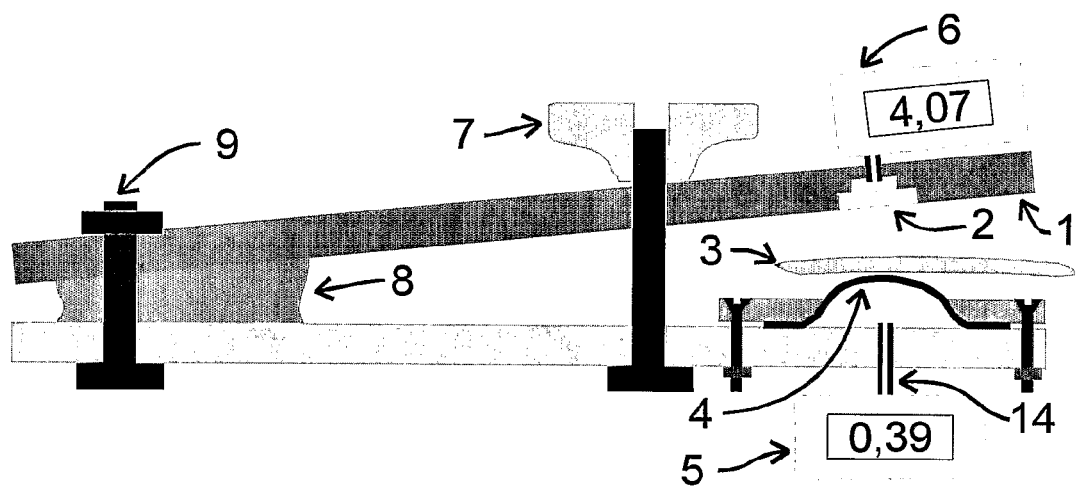
FIG. 1—Scheme of an applanation system on air permeated screen containing a chamber, pneumatic or hydraulic, for the compression application (14) during firmness measurement depending on cell's pressure.

The applanation system on air permeated screen (1) of this invention, in accordance with FIGS. 1, 2, 3, and 4, is a device for measuring cell pressure dependent firmness, according to the smallest compression necessary to cause the proper applanation of he organ against a screen (1) with porous element (2) where flows air. The compression of the leaf or planar segments is imposed by a membrane (4) until the interruption, reversible, of air flow through porous element (2). This smallest compression value is the firmness measure which causes the suitable applanation of the organ against the screen (1). The basic components of this system are:

a) Screen (1) with porous element (2) inserted or engraved.

b) A module of reference (6) for reversible indication of minimum pressure which cause the adequate sample applanation against the porous screen (2). The reference module may be engineered with an adjusted pressure gas source (1 to 5 KPa) which non interrupted flow is adjusted too. For test tips having 5 mm diameter, an air flow around 2 mL·min$^{-1}$ would be adequate. The reference module comprises a pressurized air source, for example, a mini air compressor (10), a pressure regulator (11), a restriction, register or capillar (13) and a differential pressure sensor (12). In this system, the difference of pressure through the differential pressure sensor (12) is proportional to the air flow which crosses the constriction (13), in a way the pressure difference reduces to zero when the air flow is also reduced to zero, after the interruption of air flow through screen (1). This capillar fluxmeter system may be substituted by another continuous reading fluxmeter type. The adjusted input air pressure in the pressure regulator (11) of the reference module must be of much lesser magnitude than the necessary pressures for the mechanic applanation of the organs against the screen (1).

c) The module of compression (4) and measurement (5) with which applies known pressures on the leaf, for example. This module contains membrane (4) on a chamber, containing air or other fluid, whose inner pressure is adjustable. A flexible rubber membrane (4) on the chamber enables the application of pressures uniformly adjusted on the leaf which is progressively planed against the screen (1) having porous element (2). The pressures may be adjusted by pressure regulators for compressed air cylinders in the case of air or by hydraulic system with pressure transducer if the used fluid is a liquid. For the majority of applications, pressures between 0 and 7 atmospheres are appropriate. However for specific applications different work amplitudes may be preferable.

Operation

Open up the air flow (6,14). If necessary, check up this flow value with the help of a fluxmeter or by the method of bubblemeter, i.e., with pipette, water, soap and a chronometer. Hereinafter put up the organ on the compression module, close up the screen (1) with the control lever (7) until light air flow reduction. Hereinafter apply up pressure progressively until the air flow through the porous element (2) on screen (1) is reduced to 5% or less. Hereinafter read up the pressure (4) which represents the organ firmness, which is caused by cells inside pressure, the cell turgor pressure. It is important to verify that in case pressure is reduced, the air flow must increase again, in a reversible manner.

The firmness measured by this instrument must be closer to the cells media inside pressure, not only as the cell walls are thinner, but also and as the percentage of gaseous volume before applanation is around zero, this in accordance with models of Calbo & Nery (2001) defined for cellular lattices with idealized geometry.

The strength for applanation of the organ against the screen (1) is applied with the help of the compression screen rubber (4). An important detail in the case of leaves measurement is to put the screen (1) with porous element (2) always in contact with flatter and more regular face of leaf or segmented tissue. In case the porous element (2) is a rectangle, then the length must preferentially be aligned with the vein direction. In case of using liquid fluid, in hydraulic system, the pressurization may be manual, with screw and plunger and the reading may be done with a manometer or other appropriate pressure transducer. Alternatively, in case of pneumatic system, then, the pressure adjustment and the reading may be done in common air pressure regulator.

The rectangle format with rounded edges with length of two or three times the width (for example, 6 mm×3 mm) is more appropriate than a rounded porous area of similar format. The reason for this is the facility to align the rectangle with the largest veins of the leaves. Porous elements with too elongated surface, however, may be difficult for properly applanation.

In the described system of this invention the knowledge and regularity of the porous element (2) surface area are not essentials. However, the use of porous elements (2) with a single pore or with few pores turns the reading unstable and non reproducible, and this is the reason why porous elements with too reduced area tend not to be adequate.

Construction Details

The system illustrated in FIG. 1 is a very simple and efficient way for the screen (1) utilization as one of the arms of a kind of tweezers. The spontaneous opening of this system is obtained with a rubber (8) help, or a spring. The closing, on the other hand, is done with a control lever screw set (7), which enables pressing the leaf until the air flow in the porous element is slightly reduced. The remaining measurement procedure was previously described.

The screen is preferentially put on the upper side and must be constructed with transparent material as acrylic or glass, to facilitate the appropriate positioning of the samples.

The Porous Element

Figure 3:
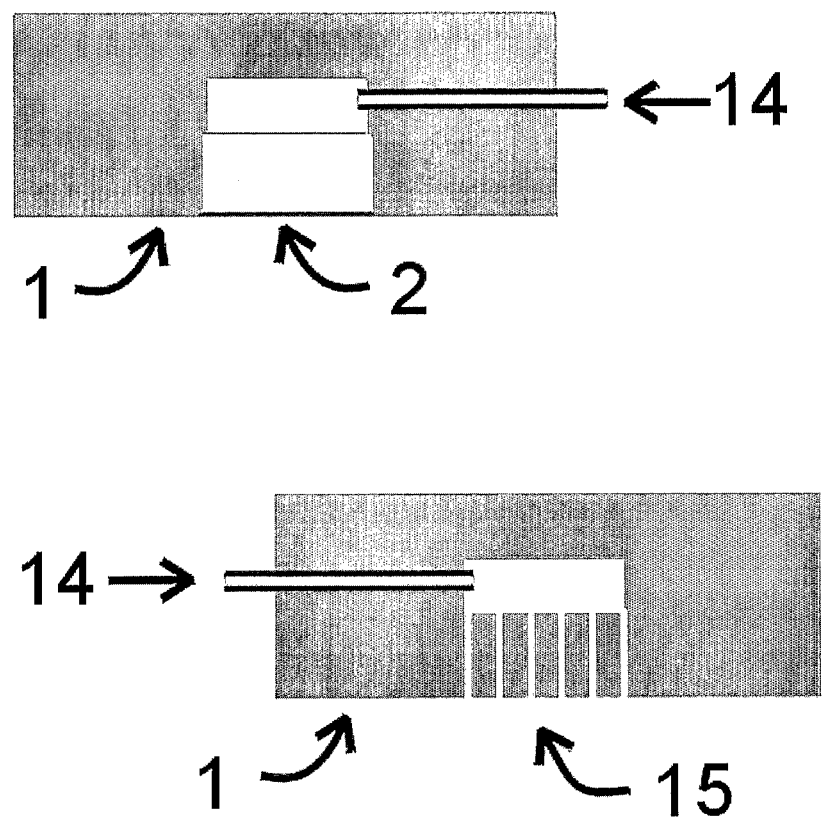
FIG. 3—Schemes of porous element types for air permeation through screen.

The porous element (2) may be a proper ceramic or simply an engraved surface with slots and holes (15), see FIG. 3. Additionally, as more sophisticated option, the porous element may contain or be mounted on a pressure transducer device to make the reading of firmness.

Membrane

The chamber with membrane (4) is possibly the most effective way to apply compression in a uniform manner on a leaf supported on the screen (1).

The membrane (4) must preferably act on the most irregular side of the leaf, because being flexible it accommodates on each irregularity, as a vein for example. Due to these accommodations the membrane can transfer the pressure almost as uniformly as a hydrostatic system could do it.

For a good coverage, the membrane area (4) must be much larger than the porous element area (2) inserted on the screen (1). This ensures a greater accuracy in the firmness measurements with this applanation technique.

Organs that can be Measured

The system proposed herein enables the measurement of leaves' firmness, from the thinnest, from plants grown up under low luminous intensity, to the thickest and laminar leaves, since they have one face with few irregularities. Such face is, in general, the upper one. Sclerified leaves, as the ones from some plants from Cerrado, once they are not soft enough, can not be measured by this type of equipment, at least for the purpose to get a firmness estimative depending on cellular interior pressure, what however don't exclude the possibility to obtain other types of interesting results but physically harder to interpret.

From some organs, like potatoes, carrots, and eggplant the system is able to measure the firmness of laminar segments of their stems, roots and fruits. This can look like a few appropriate form, but with the advent of minimally processed products measurements of this type will become each time more important for the evaluation of quality and store systems adequacy of these products.

On the field, firmness measurement depending on leaves cell turgor may be a valid biological manner of benchmark if the irrigation management, based on soil or atmosphere measurements, has been done in a manner to avoid plants from suffering of hydric stress which can harm productivity.

Air Flow in the Porous Element

Figure 2:
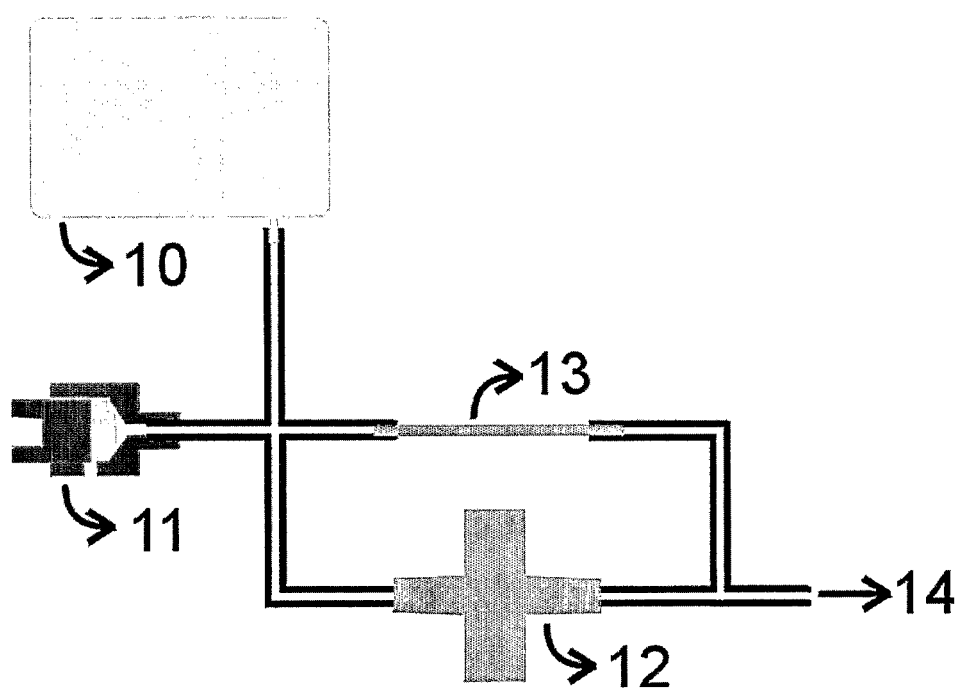
FIG. 2—Scheme of the system for air flow adjustment which can be used as reference module in the applanation system on air permeated screen.

A device shown in FIG. 2 makes use of a differential pressure transducer (12) and of a restriction (13). It is a capillar fluxmeter, in which the air pressure difference through differential pressure transducer (12) is null when the air flow is reduced to zero and maximum when air outlet (14) for the porous element (2) is completely free.

This capillar fluxmeter provides response which depends on air compressibility; however, for low pressures until 5 KPa the response is practically linear and needs no corrections.

Figure 4:
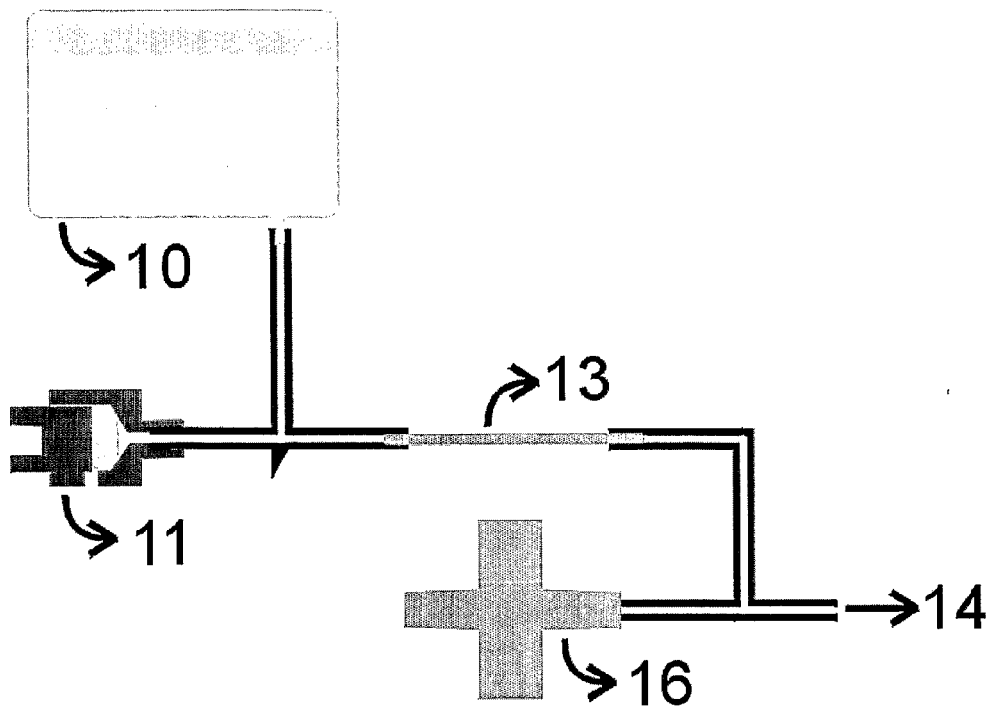
FIG. 4—Scheme of the system for air flow adjustment and measurement of it by manometer or pressure transducer.

In the system of this invention, however, other fluxmeter types may be used, among them the fluxmeter described in FIG. 4, which makes use of a simple manometer or of a "gauge" type pressure transducer.

The invention claimed is:

1. An instrument for plant material firmness evaluation comprising:
   i. a screen comprising a porous element, wherein the porous element comprises an applanation face and an applanation opposite face;
   ii. a device for detecting an obstruction to an air flow through the porous element having an air flow introducer device coupled with a fluximeter, or similar instrument, with 1 to 5 kPa pressure entry, connected to the porous element by the applanation opposite face; and
   iii. a device for plant sample applanation and plant material firmness determination through pressure measurement, positioned on the applanation face side of the screen comprising the porous element, comprising a pressure chamber that is defined at least in part by a flexible membrane screen and configured to be inflated by increasing the pressure within the pressure chamber, wherein said pressure chamber is coupled to a system for regulating and measuring the pressure within the pressure chamber; and
   iv. wherein the flexible membrane screen comprises an external surface configured to be in contact with a bottom side of a plant sample, and wherein the flexible membrane and the plant sample are compressed against the applanation face of the porous element.

2. The instrument for plant material firmness evaluation, in accordance with claim 1, wherein the porous element is composed of a ceramic material.

3. The instrument for plant material firmness evaluation, in accordance with claim 1, wherein the porous element comprises a slotted surface with several engraved micro holes configured to allow air to pass through the porous element and wherein the several engraved micro holes are linked to the device for detecting an obstruction of air flow through the porous element.

4. A process for evaluating plant material firmness comprising the following steps:
   i. activating a device configured to detect an obstruction to an air flow passing through a porous element;
   ii. placing a plant sample between a screen comprising the porous element and a membrane screen external surface, wherein the membrane screen defines, at least in part, a pressure chamber;
   iii. compressing the plant sample by pushing the screen comprising the porous element against the membrane screen until detecting a light reduction in the air flow passing through the porous element;

iv. gradually inflating the pressure chamber by activating a sample applanation and pressure measurement device, wherein as the pressure chamber inflates, the membrane screen presses the plant sample against the porous element, until the air flow through the porous element is reduced to almost zero; and v. determining the plant material firmness degree by reading an applanation pressure observed at the sample applanation and pressure measurement device.

\* \* \* \* \*